US006485514B1

(12) United States Patent
Wrenn, Jr.

(10) Patent No.: US 6,485,514 B1
(45) Date of Patent: *Nov. 26, 2002

(54) LOCAL DELIVERY OF THERAPEUTIC AGENTS

(75) Inventor: Simeon M. Wrenn, Jr., Danville, CA (US)

(73) Assignee: SuperGen, Inc., Dublin, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,281

(22) Filed: Dec. 12, 1997

(51) Int. Cl.$^7$ ................................................. A61E 2/06
(52) U.S. Cl. ...................... 623/1.42; 604/500; 604/104; 604/265; 128/898
(58) Field of Search .......................... 604/890.1, 891.1, 604/500, 502, 104, 264, 265, 523; 606/108, 192, 194; 623/1.1, 1.42, 1.46, 11, 11.11, 1.11; 424/422, 423; 128/898

(56) References Cited

U.S. PATENT DOCUMENTS

| | | | |
|---|---|---|---|
| 4,797,282 A | 1/1989 | Wahlig et al. | 424/422 |
| 5,049,132 A | 9/1991 | Shaffer et al. | 604/101 |
| 5,059,166 A | 10/1991 | Fischell et al. | 600/3 |
| 5,234,456 A * | 8/1993 | Silvestrini | 606/194 |
| 5,286,254 A | 2/1994 | Shapland et al. | 604/21 |
| 5,342,348 A | 8/1994 | Kaplan | 604/891.1 |
| 5,429,634 A | 7/1995 | Narciso, Jr. | 604/890.1 |
| 5,464,650 A | 11/1995 | Berg et al. | 427/2.3 |
| 5,500,161 A * | 3/1996 | Andrianov et al. | 264/8 |
| 5,527,337 A | 6/1996 | Stack et al. | 606/198 |
| 5,545,208 A | 8/1996 | Wolff et al. | 623/1 |
| 5,552,154 A * | 9/1996 | Giovanella et al. | 424/449 |
| 5,573,781 A | 11/1996 | Brown et al. | 424/484 |
| 5,603,722 A * | 2/1997 | Phan et al. | 606/198 |
| 5,626,862 A | 5/1997 | Brem et al. | 424/426 |
| 5,649,977 A * | 7/1997 | Campbell | 623/1 |
| 5,651,986 A | 7/1997 | Brem et al. | 424/484 |
| 5,660,851 A * | 8/1997 | Domb | 424/427 |
| 5,665,383 A | 9/1997 | Grinstaff et al. | 424/450 |
| 5,674,192 A | 10/1997 | Sahatjian et al. | 604/28 |
| 5,674,241 A * | 10/1997 | Bley et al. | 606/198 |
| 5,679,400 A | 10/1997 | Tuch | 427/2.14 |
| 5,977,163 A * | 11/1999 | Li et al. | 514/449 |
| 5,994,341 A * | 11/1999 | Hunter et al. | 514/250 |
| 6,080,751 A * | 6/2000 | Stehlin et al. | 514/283 |
| 6,111,107 A * | 8/2000 | Greenwald et al. | 546/48 |
| 6,133,416 A * | 10/2000 | Wilson et al. | 530/300 |
| 6,168,619 B1 * | 1/2001 | Dinh et al. | 623/1.13 |
| 6,191,119 B1 * | 2/2001 | Rubinfeld | 514/34 |

FOREIGN PATENT DOCUMENTS

| | | | |
|---|---|---|---|
| DE | 4028764 A1 | 12/1992 | C08G/63/08 |
| EP | 0 086 627 A1 | 8/1983 | A61K/9/00 |
| EP | 0 372 137 A1 | 6/1990 | A61M/31/00 |
| EP | 0 539 751 A1 | 5/1993 | A61K/9/00 |
| EP | 0716836 A1 | 6/1996 | |
| GB | 2 091 554 A | 4/1982 | A61K/9/00 |
| WO | WO 95/03036 | 2/1995 | A61K/9/16 |
| WO | WO 96/14834 | 5/1996 | A61K/9/22 |
| WO | WO 96/26950 | 6/1996 | C07H/15/252 |
| WO | WO96/25176 | 8/1996 | |
| WO | WO97/28165 | 8/1997 | |
| WO | WO 97/16169 | 9/1997 | A61K/9/00 |

OTHER PUBLICATIONS

Patent Abstracts of Japan, vol. 007, No. 155 (C–175), Jul. 7, 1983 & JP 58 065211 A (Mitsui Toatsu Kagaku KK), Apr. 18, 1983.

Patent Abstracts of Japan, vol. 010, No. 252 (C–369), Aug. 29, 1986, & JP 61 078718 A (Toyobo Co., Ltd.), Apr. 22, 1986.

Patent Abstracts of Japan, vol. 097, No. 003, Mar. 31, 1997 & JP 08 301762 A (Teijin Ltd.), Nov. 19, 1996.

Patent Abstracts of Japan, vol. 098, No. 005, Apr. 30, 1998 & JP 10 017472 A (Yakult Honsha Co., Ltd. et al.), Jan. 20, 1998.

"Angiotech Makes First Step on Drug Approval Path", URL http://www.library.ubc.ca/patscan/bur.html.

Mathew, AE et al., "Synthesis and evaluation of some water–soluble prodrugs and derivatives of taxol with anti-tumor activity", *J. Med. Chem*, Jan., 35:1, 145–51 (1992) (Abstract).

Greenwald, RB et al. "Drug delivery systems: water soluble taxol 2'–poly(ethylene glycol) ester prodrugs–design and in vivo effectiveness", *J. Med. Chem.*,39:2, 424–31 (1996) (Abstract).

Li, C et al., "Synthesis, biodistribution and imaging properties of indium–111–DTPA–paclitaxel in mice bearing mammary tumors", *J. Nucl Med.*, 38:7, 1042–7 (1997) (Abstract).

Li, C et al., "Synthesis and evaluation of water–soluble polyethylene glycol–paclitaxel conjugate as a paclitaxel prodrug", *Anticancer Drugs*, 7:6, 642–8 (1996) (Abstract).

Georg GI et al., "Synthesis of biologically active taxol analogues with modified phenylisoserine side chains", *J. Med. Chem*. 35:22, 4230–7 (1992) (Abstract).

(List continued on next page.)

Primary Examiner—Brian L. Casler
Assistant Examiner—Cris L. Rodriguez
(74) Attorney, Agent, or Firm—Shirley Chen; Wilson Sonsini Goodrich & Rosati

(57) ABSTRACT

Disclosed are implants, stents, catheters, methods and kits for the local delivery of therapeutic agents that are preferentially cytotoxic or cytostatic with regards to proliferating cells to sites where proliferative cells are present.

5 Claims, No Drawings

OTHER PUBLICATIONS

Mamber SW, et al., "Tubulin polymerization by paclitaxel (taxol) phosphate prodrugs after metabolic activation with alkaline phosphatase", *J. Pharmacol. Exp. Ther.*, 274:2, 877–83 (1995) (Abstract).

Grover S., et al. "Differential effects of paclitaxel (Taxol) analogs modified at positions C–2, C–7, and C–3' on tubulin polymerization and polymer stabilization:identification of a hyperactive paclitaxel derivative", *Biochemistry*, 34:12, 3927–34, (1995) (Abstract).

Senter, Peter D. et al., "The Role of Rat Serum Carboxylesterase in the Activation of Paclitaxel and Camptothecin Prodrugs", *Cancer Research*, 1471–1474 (1996).

Pantazis, P. et al., "The Camptothecins From Discovery to the Patient," *Annals of the New York Academy of Sciences*, vol. 803 (1996).

Burke, T. "Chemistry of the Camptothecins in the Bloodstream," *Annals of the New York Academy of Sciences*, vol. 803 (1996).

Liu, Leroy F., et al., "Mechanism of Action of Camptothecin," *Annals of the New York Academy of Sciences*, vol. 803 (1996).

Darzynkiewicz, Z., et al., "The Cell Cycle Effects of Camptothecin," *Annals of the New York Academy of Sciences*, vol. 803 (1996).

Traganos, F. et al. "Induction of Apoptosis by Camptothecin and Topotecan," *Annals of the New York Academy of Sciences*, vol. 803 (1996).

Chatterjee, D. et al., "Induction of Apoptosis in Malignant and Camptothecin–resistant Human Cells," *Annals of the New York Academy of Sciences*, vol. 803 (1996).

* cited by examiner

LOCAL DELIVERY OF THERAPEUTIC AGENTS

BACKGROUND OF THE INVENTION

1. Field of the Invention

The present invention relates to the local delivery of therapeutic agents that are preferentially cytotoxic or cytostatic with regards to proliferating cells.

2. Description of Related Art

Uncontrolled cell proliferation can be a serious problem. For example, one form of uncontrolled cell proliferation is cancer, which is second only to cardiac disease as a cause of death in the United States. Another form of uncontrolled cell proliferation is restenosis, which can be life threatening if not treated.

Researchers have developed a series of therapeutic agents for systemic treatment of cancer. Two therapeutic agents of interest are camptothecin and taxol.

20(S)-camptothecin (CPT), a plant alkaloid, was found to have anticancer activity in 1966 (Wall, M., Wani, M. C., Cooke, C. E., Palmer, K. H., McPhail, A. T. and Slim, G. A. "Plant antitumor agents. I. The isolation and structure of camptothecin, a novel alkaloidal leukemia and tumor inhibitor from *Camptotheca acuminata*", J. Am. Chem. Soc. 88: 3888–3890, 1966).

During the sixties and seventies the sodium salt of CPT was derived from CPT, and clinical trials of this chemically altered CPT were carried out and then abandoned because of the high toxicity and low potency of this compound (Gottlieb, J. A., Guarino, A. M., Call, J. B., Oliverio, V. T. and Block, J. B. "Preliminary pharmacological and clinical evaluation of camptothecin sodium salt (NSC 100880)", *Cancer Chemother. Rep.* 54: 461–470; 1979; Muggia, F. M., Creaven, P. J., Hansen, H. H., Cohen, M. N. and Selawry, D. S. "Phase I clinical trials of weekly and daily treatment with camptothecin (NSC 100880). Correlation with clinical studies." *Cancer Chemother. Rep.* 56: 515–521; 1972; Gottlieb, J. A. and Luce, J. K. "Treatment of malignant melanoma with camptothecin (NSC 100880)." *Cancer Chemother. Rep.* 56: 103–105; 1972; and Moertel, C. G., Schutt, A. J., Reitemeier, R. J. and Hahn, R. G. "Phase II study of camptothecin (NSC 100880) in the treatment of advanced gastrointestinal cancer." *Cancer Chemother Rep.* 56: 95–101; 1972.

All these trials were conducted using the hydrosoluble, sodium salt derivative of CPT (CPT Na+), which was administered intravenously. The net result of this research established the ineffectiveness and the toxicity of CPT Na+.

Drug therapies have been evaluated with respect to treating human cancer, e.g., human cancer xenograft lines. Human tumors are serially heterotransplanted into immunodeficient, so-called "nude" mice, and the mice then tested for their responsiveness to a specific drug. (Giovanella, B. C., et al., *Cancer* 52(7): 1146(1983)). The data obtained in these studies strongly support the validity of heterotransplanted human tumors into immunodeficient mammals, such as nude mice, as a predictive model for testing the effectiveness of anticancer agents.

It was determined that 9-Amino-20(S)-Camptothecin (9AC) and 10,11-Methylendioxy-20(S)-Camptothecin (10, 11 MD) are capable of having high anticancer activity against human colon cancer xenografts (Giovanella, B. C., Wall, M. E., Wani, M. C. Nicholas, A. W., Liu, L. F., Silber, R. and Potmesil, M. "Highly effective topoisomerase-I targeted chemotherapy of human colon cancer in xenografts." *Science* 246: 1046–1048; 1989).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

However, these methods of administration are all systemic, and therefore can create undesirable systemic side-effects.

Taxol is a naturally occurring compound which has shown promise as an anti-cancer drug. For example, taxol has been found to be an active agent against drug-refractory ovarian cancer by McGuire et al. See "Taxol: A Unique Anti-Neoplastic Agent With Significant Activity Against Advanced Ovarian Epithelial Neoplasms." *Ann. Int. Med.,* 111. 273–279 (1989).

Unfortunately, taxol has extremely low solubility in water, which makes it difficult to provide a suitable dosage form. In fact, in Phase I clinical trials, severe allergic reactions were caused by the emulsifiers administered in conjunction with taxol to compensate for taxol's low water solubility; at least one patient's death was caused by an allergic reaction induced by the emulsifiers. Dose limiting toxicities include neutropenia, peripheral neuropathy, and hypersensitivity reactions.

These investigations showed that systemic administration of taxol can result in severe systemic side-effects, which limits the usefulness of taxol in a clinical setting.

Furthermore, the investigations into CPT and taxol, as discussed above, focused primarily on the use of these materials as anti-cancer agents. By way of comparison, fairly little work has been done with these materials in the area of restenotic lesions.

Restenosis may be defined as the reclosure of a previously stenosed and subsequently dilated peripheral or coronary vessel. It may occur at a rate of 20–50% for these procedures and is dependent on a number of clinical and morphological variables. Restenosis may begin shortly after a stenosing procedure, and tends to cease after about 4–12 months thereafter. Several hypotheses exist on why and how restenosis occurs. Some researchers believe that restenosis is a natural healing process in response to the injury that occurs during a stenosing procedure. The problem associated with this healing process is that, in some instances, it does not shut off. the artery continues to "heal" until it becomes occluded by proliferating cells.

Unfortunately, there has been only marginal success in the treatment of restenosis, particularly in the area of restenosis of coronary arteries.

There is therefore a need for apparatus, methods and kits for the treatment of proliferating cells, such as cancerous or restenotic cells, to resolve the aforementioned problems.

SUMMARY OF THE INVENTION

This invention relates to implants for administering at least one therapeutic agent that is preferentially cytotoxic or cytostatic with regards to proliferating cells comprising an implant structure and at least one therapeutic agent that is preferentially cytotoxic or cytostatic with regards to proliferating cells.

In another aspect, this invention relates to stents comprising at least one therapeutic agent that is preferentially cytotoxic or cytostatic with regards to proliferating cells. Additionally, this invention relates to a method of treatment comprising inserting a stent into a lumen of a body, wherein the stent comprises at least one therapeutic agent that is preferentially cytotoxic or cytostatic with regards to proliferating cells.

In still another aspect, the invention relates to an apparatus comprising an intraluminal catheter and a supply of at least one therapeutic agent that is preferentially cytotoxic or cytostatic with regards to proliferating cells. Additionally, the invention relates to an apparatus comprising a container adaptable for connection to an intraluminal catheter, wherein the container contains at least one therapeutic agent that is preferentially cytotoxic or cytostatic with regards to proliferating cells.

Furthermore, the invention relates to a method of treatment comprising administering at least one therapeutic agent that is preferentially cytotoxic or cytostatic with regards to proliferating cells through an intraluminal catheter. In addition, the invention relates to a kit comprising a container adaptable for connection to an intraluminal catheter, wherein the container contains at least one therapeutic agent that is preferentially cytotoxic or cytostatic with regards to proliferating cells.

DETAILED DESCRIPTION OF THE INVENTION

In one aspect, the invention relates to an implant for administering at least one therapeutic agent that is preferentially cytotoxic or cytostatic with regards to proliferating cells comprising an implant structure and at least one therapeutic agent that is preferentially cytotoxic or cytostatic with regards to proliferating cells. Additionally, the invention relates to implants where the implant is a time-release implant, or is a gel or polymer implant.

In yet another aspect, the invention concerns implants where the therapeutic agents comprise agents that interrupt cell replication and those that prevent or limit chemotaxis. In a further aspect, the invention concerns implants where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention additionally relates to implants where the therapeutic agent comprises methotrexate, its physiologically tolerated salts, and derivatives, analogs, mixtures and conjugates thereof. Further, the invention relates to implants where the therapeutic agent comprises mitoxantrone, its physiologically tolerated salts, and derivatives, analogs, mixtures and conjugates thereof. Additionally, the invention concerns implants wherein the at least one therapeutic agent is camptothecin, its physiologically tolerated salts, and derivatives, analogs, mixtures and conjugates thereof or functional equivalents thereof.

In still another aspect, the invention relates to implants wherein the therapeutic agent is camptothecin. In addition, the invention concerns implants wherein the therapeutic agent is 9-nitro-20(S) camptothecin. In yet another aspect, the invention concerns implants wherein the therapeutic agent is 9-amino-20(S) camptothecin.

The invention also concerns implants wherein the at least one therapeutic agent is taxol, its physiologically tolerated salts, and derivatives, analogs, mixtures and conjugates thereof or functional equivalents thereof. Further, the invention concerns implants where the implant is coated and the therapeutic agent is contained in the coating. In addition, the invention concerns implants where the therapeutic agent is contained within the implant structure.

In another aspect, the invention relates to implants wherein the therapeutic agent is present in an amount effective to reduce cell proliferation once the implant is deployed. Furthermore, the invention relates to implants where the cell proliferation that is reduced is restenotic or cancerous. In other aspects, the invention is relates to implants where the implant is biodegradable or is formed in situ.

Additionally, the invention concerns methods of treatment comprising inserting an implant into a lumen in a body wherein the implant is the implant disclosed above. Furthermore, the invention concerns these methods where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

In an aspect, the invention relates to these methods where the therapeutic agent comprises methotrexate, its physiologically tolerated salts, and derivatives, analogs, mixtures and conjugates thereof. In another aspect, the invention relates to these methods where the therapeutic agent comprises mitoxantrone, its physiologically tolerated salts, and derivatives, analogs, mixtures and conjugates thereof.

Furthermore, the invention concerns these methods wherein the at least one therapeutic agent is camptothecin, its physiologically tolerated salts, and derivatives, analogs, mixtures and conjugates thereof or functional equivalents thereof. In still another aspect, the invention concerns these methods wherein the therapeutic agent is camptothecin. Additionally, the invention relates to these methods wherein the therapeutic agent is 9-nitro-20(S) camptothecin. Further, the invention concerns these methods wherein the therapeutic agent is 9-amino-20(S) camptothecin. In still another aspect, the invention concerns these methods wherein the at least one therapeutic agent is taxol, its physiologically tolerated salts, and derivatives, analogs, mixtures and conjugates thereof or functional equivalents thereof.

Additionally, the invention concerns these methods where the therapeutic agent is contained within the stent structure. In another aspect, the invention relates to these methods wherein the therapeutic agent is present in an amount effective to reduce cell proliferation once the stent is deployed. In still another aspect, the invention relates to these methods where the cell proliferation that is reduced is restenotic or cancerous.

Further, the invention concerns these methods where the methods are used to treat restenosis, various types of cancers, insults to body tissue due to surgery, diseases that produce fibrosis of tissue, repetitive motion disorders, disorders of tissues that are not highly vascularized, and proliferative responses associated with organ transplants.

Additionally, the invention concerns these methods where the methods are used to treat coronary, carotid, and cerebral restenotic lesions. In still another aspect, the invention relates to these methods where the methods are used to treat gliomas, other central nervous system tumors, tumors at localized sites including inoperable tumors, tumors where localized treatment of tumors would be beneficial, and solid tumors. In an aspect of the invention, these methods are disclosed as useful to treat cell proliferation associated with joint surgery, bowel surgery, and cheloid scarring. In another aspect of the invention, these methods are disclosed as useful to treat emphysema. In still another aspect, the invention relates to these methods where the methods are used to treat carpal tunnel syndrome. Further, the invention is concerned with these methods where the methods are used to treat disorders of tissues that are not highly vascularized. Additionally, the invention relates to these methods where the methods are used to treat proliferative responses contributing to potential organ rejections or associated complications. Further, the invention concerns the methods where the method is used to treat proliferative responses occurring as a result of transplantation of the heart, lung, liver, kidney, and other body organs or organ systems.

In addition, the invention concerns a kit comprising an implant and a mechanism capable of inserting the implant into a lumen of a body, wherein the implant is the implant as disclosed above. In an aspect, the invention relates to these kits wherein the mechanism is an intraluminal catheter. In another aspect, the invention concerns these kits where the therapeutic agents comprise agents that interrupt cell replication and those that prevent or limit chemotaxis. In still another aspect, the invention relates to these kits where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to these kits where the therapeutic agent comprises methotrexate, its physiologically tolerated salts, and derivatives, analogs, mixtures and conjugates thereof. The invention further relates to these kits where the therapeutic agent comprises mitoxantrone, its physiologically tolerated salts, and derivatives, analogs, mixtures and conjugates thereof. The invention also relates to these kits wherein the at least one therapeutic agent is camptothecin, its physiologically tolerated salts, and derivatives, analogs, mixtures and conjugates thereof or functional equivalents thereof. The invention additionally relates to these kits wherein the therapeutic agent is camptothecin. The invention also relates to these kits wherein the therapeutic agent is 9-nitro-20(S) camptothecin. The invention also relates to these kits wherein the therapeutic agent is 9-amino-20(S) camptothecin.

The invention additionally relates to these kits wherein the at least one therapeutic agent is taxol, its physiologically tolerated salts, and derivatives, analogs, mixtures and conjugates thereof or functional equivalents thereof. The invention also relates to these kits where the implant is coated and the therapeutic agent is contained in the coating.

The invention also relates to these kits where the therapeutic agent is contained within the implant structure. The invention also relates to these kits wherein the therapeutic agent is present in an amount effective to reduce cell proliferation once the implant is deployed. The invention also relates to these kits where the cell proliferation that is reduced is restenotic or cancerous. The invention also relates to these kits where the stent is biodegradable or is formed in situ.

In another aspect, the invention relates to a stent comprising at least one therapeutic agent that is preferentially cytotoxic or cytostatic with regards to proliferating cells. The invention also relates to these stents where the therapeutic agents comprise agents that interrupt cell replication and those that prevent or limit chemotaxis. The invention also relates to these stents where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to these stents where the therapeutic agent comprises methotrexate, its physiologically tolerated salts, and derivatives, analogs, mixtures and conjugates thereof. The invention also relates to these stents where the therapeutic agent comprises mitoxantrone, its physiologically tolerated salts, and derivatives, analogs, mixtures and conjugates thereof.

The invention also relates to these stents wherein the at least one therapeutic agent is camptothecin, its physiologically tolerated salts, and derivatives, analogs, mixtures and conjugates thereof or functional equivalents thereof. The invention further relates to these stents wherein the therapeutic agent is camptothecin. The invention also relates to these stents wherein the therapeutic agent is 9-nitro-20(S) camptothecin. The invention also relates to these stents wherein the therapeutic agent is 9-amino-20(S) camptothecin.

In another aspect, the invention concerns these stents wherein the at least one therapeutic agent is taxol, its physiologically tolerated salts, and derivatives, analogs, mixtures and conjugates thereof or functional equivalents thereof. Further, the invention relates to these stents where the stent is coated and the therapeutic agent is contained in the coating. The invention also relates to these stents where the therapeutic agent is contained within the stent structure. The invention also relates to these stents wherein the therapeutic agent is present in an amount effective to reduce cell proliferation once the stent is deployed. The invention also relates to these stents where the cell proliferation that is reduced is restenotic or cancerous. The invention also relates to these stents where the stent is biodegradable or is formed in situ.

In another aspect, the invention relates to methods of treatment comprising inserting a stent into a lumen of a body, wherein the stent comprises at least one therapeutic agent that is preferentially cytotoxic or cytostatic with regards to proliferating cells. The invention also relates to these methods where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to these methods where the therapeutic agent comprises methotrexate, its physiologically tolerated salts, and derivatives, analogs, mixtures and conjugates thereof. The invention also relates to these methods where the therapeutic agent comprises mitoxantrone, its physiologically tolerated salts, and derivatives, analogs, mixtures and conjugates thereof. The invention also relates to these methods wherein the at least one therapeutic agent is camptothecin, its physiologically tolerated salts, and derivatives, analogs, mixtures and conjugates thereof or functional equivalents thereof. The invention also relates to these methods wherein the therapeutic agent is camptothecin. The invention also relates to these methods wherein the therapeutic agent is 9-nitro-20(S) camptothecin. The invention also relates to these methods wherein the therapeutic agent is 9-amino-20(S) camptothecin.

The invention also relates to these methods wherein the at least one therapeutic agent is taxol, its physiologically tolerated salts, and derivatives, analogs, mixtures and conjugates thereof or functional equivalents thereof. The invention-also relates to these methods where the therapeutic agent is contained within the stent structure. The invention also relates to these methods wherein the therapeutic agent is present in an amount effective to reduce cell proliferation once the stent is deployed. The invention also relates to these methods where the cell proliferation that is reduced is restenotic or cancerous.

The invention also relates to these methods where the method is used to treat restenosis, various types of cancers, insults to body tissue due to surgery, diseases that produce fibrosis of tissue, repetitive motion disorders, disorders of tissues that are not highly vascularized, and proliferative responses associated with organ transplants. The invention also relates to these methods where the method is used to treat coronary, carotid, and cerebral restenotic lesions. The invention also relates to these methods where the method is used to treat gliomas, other central nervous system tumors, tumors at localized sites including inoperable tumors, tumors where localized treatment of tumors would be beneficial, and solid tumors.

The invention also relates to these methods where the method is used to treat cell proliferation associated with joint surgery, bowel surgery, and cheloid scarring. The invention also relates to these methods where the method is used to treat emphysema. The invention also relates to these methods where the method is used to treat carpal tunnel syndrome. The invention also relates to these methods where the method is used to treat disorders of tissues that are not highly vascularized. The invention also relates to these methods where the method is used to treat proliferative responses contributing to potential organ rejections or associated complications.

The invention also relates to these methods where the method is used to treat proliferative responses occurring as a result of transplantation of the heart, lung, liver, kidney, and other body organs or organ systems. The invention also relates to these methods where the stent is biodegradable or is formed in situ.

The invention also relates to kits comprising a stent and a mechanism capable of introducing the stent into a lumen of a body, wherein the stent is the stent disclosed above. In another aspect, the invention relates to these kits wherein the mechanism is an intraluminal catheter. The invention also relates to these kits where the therapeutic agents comprise agents that interrupt cell replication and those that prevent or limit chemotaxis.

The invention also relates to these kits where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to these kits where the therapeutic agent comprises methotrexate, its physiologically tolerated salts, and derivatives, analogs, mixtures and conjugates thereof. The invention also relates to these kits where the therapeutic agent comprises mitoxantrone, its physiologically tolerated salts, and derivatives, analogs, mixtures and conjugates thereof. The invention also relates to these kits wherein the at least one therapeutic agent is camptothecin, its physiologically tolerated salts, and derivatives, analogs, mixtures and conjugates thereof or functional equivalents thereof.

The invention also relates to these kits wherein the therapeutic agent is camptothecin. The invention also relates to these kits wherein the therapeutic agent is 9-nitro-20(S) camptothecin. The invention also relates to these kits wherein the therapeutic agent is 9-amino-20(S) camptothecin.

The invention also relates to these kits wherein the at least one therapeutic agent is taxol, its physiologically tolerated salts, and derivatives, analogs, mixtures and conjugates thereof or functional equivalents thereof.

The invention also relates to these kits where the stent is coated and the therapeutic agent is contained in the coating. The invention also relates to these kits where the therapeutic agent is contained within the stent structure. The invention also relates to these kits wherein the therapeutic agent is present in an amount effective to reduce cell proliferation once the stent is deployed. The invention also relates to these kits where the cell proliferation that is reduced is restenotic or cancerous. The invention also relates to these kits where the stent is biodegradable or is formed in situ.

In another aspect, the invention relates to an apparatus comprising an intraluminal catheter and a supply of at least one therapeutic agent that is preferentially cytotoxic or cytostatic with regards to proliferating cells. The invention also relates to the apparatus comprising a container adaptable for connection to an intraluminal catheter, wherein the container contains at least one therapeutic agent that is preferentially cytotoxic or cytostatic with regards to proliferating cells.

The invention also relates to the apparatus where the therapeutic agents comprise agents that interrupt cell replication and those that prevent or limit chemotaxis. The invention also relates to the apparatus where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to the apparatus where the therapeutic agent comprises methotrexate, its physiologically tolerated salts, and derivatives, analogs, mixtures and conjugates thereof. The invention also relates to the apparatus where the therapeutic agent comprises mitoxantrone, its physiologically tolerated salts, and derivatives, analogs, mixtures and conjugates thereof.

The invention also relates to the apparatus wherein the at least one therapeutic agent is camptothecin, its physiologically tolerated salts, and derivatives, analogs, mixtures and conjugates thereof or functional equivalents thereof. The invention also relates to the apparatus wherein the therapeutic agent is camptothecin. The invention also relates to the apparatus wherein the therapeutic agent is 9-nitro-20(S) camptothecin. The invention also relates to the apparatus wherein the therapeutic agent is 9-amino-20(S) camptothecin.

The invention also relates to the apparatus wherein the at least one therapeutic agent is taxol, its physiologically tolerated salts, and derivatives, analogs, mixtures and conjugates thereof or functional equivalents thereof.

The invention also relates to a method of treatment comprising administering at least one therapeutic agent that is preferentially cytotoxic or cytostatic with regards to proliferating cells through an intraluminal catheter. The invention also relates to this method where the therapeutic agent comprises at least one of camptothecin, taxol, methotrexate, mitoxantrone, etoposide, colchicine, azathioprine, vincristine, vinblastine, fluorouracil, adriamycin and mitomycin, their physiologically tolerated salts, and derivatives, analogs, mixtures and conjugates thereof.

The invention also relates to this method where the therapeutic agent comprises methotrexate, its physiologically tolerated salts, and derivatives, analogs, mixtures and conjugates thereof. The invention also relates to this method where the therapeutic agent comprises mitoxantrone, its physiologically tolerated salts, and derivatives, analogs, mixtures and conjugates thereof.

The invention also relates to this method wherein the at least one therapeutic agent is camptothecin, its physiologically tolerated salts, and derivatives, analogs, mixtures and conjugates thereof or functional equivalents thereof. The invention also relates to this method wherein the therapeutic agent is camptothecin. The invention also relates to this method wherein the therapeutic agent is 9-nitro-20(S) camptothecin. The invention also relates to this method wherein the therapeutic agent is 9-amino-20(S) camptothecin.

The invention also relates to this method wherein the at least one therapeutic agent is taxol, its physiologically tolerated salts, and derivatives, analogs, mixtures and conjugates thereof or functional equivalents thereof.

The invention also relates to this method where the method is used to treat restenosis, various types of cancers, insults to body tissue due to surgery, diseases that produce fibrosis of tissue, repetitive motion disorders, disorders of tissues that are not highly vascularized, and proliferative responses associated with organ transplants.

The invention also relates to this method where the method is used to treat coronary, carotid, and cerebral restenotic lesions. The invention also relates to this method where the method is used to treat gliomas, other central nervous system tumors, tumors at localized sites including inoperable tumors, tumors where localized treatment of tumors would be beneficial, and solid tumors. The invention also relates to this method where the method is used to treat cell proliferation associated with joint surgery, bowel surgery, and cheloid scarring. The invention also relates to this method where the method is used to treat emphysema. The invention also relates to this method where the method is used to treat carpal tunnel syndrome. The invention also relates to this method where the method is used to treat disorders of tissues that are not highly vascularized.

The invention also relates to this method where the method is used to treat proliferative responses contributing to potential organ rejections or associated complications. The invention also relates to this method where the method is used to treat proliferative responses occurring as a result of transplantation of the heart, lung, liver, kidney, and other body organs or organ systems.

Further, this invention relates to a kit comprising a container adaptable for connection to an intraluminal catheter, wherein the container contains at least one therapeutic agent that is preferentially cytotoxic or cytostatic with regards to proliferating cells.

The inventor has unexpectedly discovered that uncontrolled cell proliferation can be controlled by administering therapeutic agents in a localized fashion, rather than systemically. Such localized administration allows for minimization of side effects as compared to systemic administration of the therapeutic agents. In the context of this invention, cell proliferation covers a broad range of uncontrolled cellular growth including, but not limited to chemotaxis and replication.

Specific cell proliferative indications that may be treated using this invention include restenosis, various types of cancers such as primary tumors, insults to body tissue due to surgery, diseases that produce fibrosis of tissue, repetitive motion disorders, disorders of tissues that are not highly vascularized, and proliferative responses associated with organ transplants.

Specific types of restenotic lesions that can be treated using the present invention include coronary, carotid, and cerebral lesions. Specific types of cancers that can be treated using this invention include gliomas, other central nervous system tumors or tumors at localized sites including inoperable tumors or in tumors where localized treatment of tumors would be beneficial, and solid tumors. Treatment of cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

A number of therapeutic agents can be used in the practice of this invention. Among those are agents that interrupt cell replication and those that prevent or limit chemotaxis. Examples of suitable agents include those that interfere with cell mitosis and those that interfere with DNA synthesis. Particular agents that may be used in the practice of this invention include camptothecin (CPT), taxol, methotrexate, mitoxantrone, etoposide, colchicine, azathioprine, vincristine, vinblastine, fluorouracil, rhizoxin, adriamycin and mitomycin, their physiologically tolerated salts, and derivatives, analogs, and conjugates thereof. Derivatives and analogs are defined to include prodrugs as well.

Any of the agents suitable for use in this invention may also be combined with other agents in a physiologically acceptable manner. This combination can peformed simultaneously (i.e. as a drug "cocktail"), sequentially, or a mixture of simultaneous and sequential therapies.

Two of therapeutic agents that may be used in this invention, CPT and taxol, are of particular interest.

Camptothecin is a plant alkaloid isolated from *Camptotheca acuminata*. While not wishing to be bound by any particular mechanism of action, the inventor believes that the following scientific information may be useful in understanding how camptothecin might achieve its effects. Studies on the mechanism of action of camptothecin and related compounds suggested that they may inhibit the enzyme topoisomerase I. Inhibition of this enzyme may result in inhibited DNA synthesis and may cause DNA strand breaks. Y-H. Hsiang et al., Cancer Res. 49:5077–5082 (1989). This document and all other documents specifically cited in this application are incorporated by reference as if reproduced in full herein.

It has also been suggested that the complex of DNA and topoisomerase I was stabilized by camptothecin, preventing reannealing of DNA, but still allowing the cleavage of the DNA strand. Id. Studies of camptothecin and its analogs suggested that only the compounds that inhibited topoisomerase I were active. In contrast, those analogs that did not inhibit topoisomerase I were inactive as inhibitors of cell proliferation in the L1210 cell line. Y-H Hsiang et al., Proc. Am. Assoc. Cancer Res. 30:622 (1989) (Abstract).

Overall, these activities suggest the underpinnings for cytotoxic and/or cytostatic effects with greater activity against proliferating cells than quiescent or normal cells. See also P. Pantazis et al., *Complete inhibition of growth followed by death of human malignant melanoma cells in vitro and regression of human melanoma xenografts in immunodeficient mice induced by camptothecins,* Cancer Res. 52:3980–3987 (1992); P. Pantazis et al., *Regression of human breast carcinoma tumors in immunodeficient mice treated with 9-nitrocamptothecin: differential response of nontumorigenic and tumorigenic human breast cancer cells in vitro,* Cancer Res. 53:1577–1582 (1993); P. Pantazis et al., *Camptothecin derivatives induce regression of human ovarian non-tumorigenic and tumorigenic cells in vitro,* Int. J. Cancer 53:863–871 (1993).

Chemical derivatives of CPT can be prepared either in a semisynthetic or totally synthetic way. (See, e.g., Wani, M. C. et al., *J. Med. Chem.* 23:544, 1980; Wani, M. C. et al., *J. Med. Chem.* 30:2317 (1987). Camptothecin Sodium Salt (CPT Na+), 9-Nitro-20(S)-Camptothecin ($9NO_2$) and 9-Amino-20(S)-Camptothecin (9AC) can also be synthesized from CPT. CPT and derivatives thereof usually are extensively purified prior to administering for use in the present invention because: (1) the natural product contains several other components which have a large degree of toxicity, and (2) FDA regulations require such purifying for any drug or compound to be used as a medicine. Methods of purification known by those skilled in the art can be used, e.g.—dissolving the CPT in a suitable solvent such as chloroform or methylene chloride and then adsorbing onto a column containing silica gel and then carrying out elution of the adsorbed materials by increasing the polarity of the eluant by adding, e.g., methanol.

The purity of the compound can be tested by high performance liquid chromatography (HPLC) and thin layer chromatography (TLC) and other appropriate methods known in the art. The compound can also be completely characterized using infrared (IR), ultraviolet (UV) and nuclear magnetic resonance (NMR) spectroscopy and elemental analysis.

Furthermore, the CPT and derivatives thereof used in the present invention are water-insoluble and not administered in the chemically and physically different sodium salt form. This difference can easily be observed by looking at their elemental analysis, NMR, UV and IR spectra and also by their different physical behavior in HPLC and TLC experiments.

The derivatives of CPT for use in the present invention include, for example, $9NO_2$-20(S) (aka 9NC), and 9AC-20(S). Other related derivatives may also be used in conjunction with the method of the present invention. Examples include dimethylaminomethyl-10-hydroxy-20(S)-CPT (topotecan), 7-ethyl-10-[4-(1-piperdino)-1-piperdino]-carbonyloxy-CPT (CPT-11), 7-ethyl-10-hydroxy-20(S)-CPT, 9-amino-CPT, 9-nitro-CPT, 10,11-methylenedioxy-20(S)-CPT, 9-chloro-20(S)-CPT, 9-bromo-20(S)-CPT, 9-hydroxy-20(S)-CPT, 11-hydroxy-20(S)CPT, and 10-hydroxy-20(S)-CPT. Additionally, the camptothecin derivatives disclosed in WO 97/28165 (Zhisong, et al.) may be used in the practice of this invention.

Use of taxol for systemic treatment of cancer has been reasonably extensive. While not wishing to be bound by any particular mechanism of action, the inventor believes that the following scientific information may be useful in understanding how taxol might achieve its effects. Studies on the mechanism of action of taxol and its derivatives suggest that it promotes microtubule formation from tubulin and stabilizes microtubules by preventing depolymerization. M. A. Jordan et al. Proc. Natl. Acad. Sci. USA, 90:9552–9556 (1993). This stabilization may interfere with the normal microtubule reorganization that is essential for cell division and may result in mitotic arrest of dividing cells. The may prevent cell division in proliferating cells. In many cell types, apoptosis and cytotoxic effects may also be demonstrated. These effects may lead to beneficial effects in diseases such as cancer or other cell proliferative diseases such as restenosis, where selective activity against proliferative versus normal cells has been suggested.

The side effect profiles of taxols administered systemically have been investigated previously. Brown et al., in "A Phase I Trial of Taxol Given By A 6-Hour Intravenous Infusion" *J. of Clin. Oncol.,* Vol. 9, No. 7. pp. 1261–1267 (July, 1991) report on a Phase I Trial in which taxol was provided as a 6-hour IV infusion every 21 days without premedication. 31 patients received 64 assessable courses of taxol. One patient had a severe (or acute) hypersensitivity reaction, which required discontinuation of the infusion and immediate treatment to save the patients life. Another patient experienced a hypersensitivity reaction, but it was not so severe as to require discontinuing the infusion. Myelosuppression was dose-limiting, with 2 fatalities due to sepsis. Non-hematologic toxicity was of Grade 1 and 2, except for one patient with grade 3 mucositis and 2 patients with Grade 3 neuropathy. The neuropathy consisted of reversible painful paresthesias, requiring discontinuation of taxol in two patients. Four partial responses were seen (3 in patients with non-small-cell lung cancer, and one in a patient with adenocarcinoma of unknown primary). The maximum tolerated dose reported was 275 $mg/m^2$, and the recommended Phase II starting dose was 225 $mg/m^2$. The incidence of hypersensitivity reaction was reported to be schedule-dependent with 6 to 24-hour infusions of drug having a 0% to 8% incidence of hypersensitivity reactions. It was also reported that hypersensitivity reactions persist with or without premedication despite prolongation of infusion times. Since these Phase I studies were conducted on terminally ill patients suffering from a variety of cancers, the efficacy of the taxol treatments could not be determined.

In a study by Kris et al., taxol formulated with Cremaphor EL in dehydrated alcohol was given as a 3-hour IV infusion every 21 days, with the administered dosage ranging from 15 to 230 $mg/m^2$ in nine escalation steps. Kris et al. concluded that "with the severity and unpredictability of the hypersensitivity reactions, further usage of taxol is not indicated with this drug formulation on this administration schedule." See *Cancer Treat. Rep.,* Vol. 70, No. 5, May 1986.

Since early trials using a bolus injection or short (1–3 hour) infusions induced anaphylactic reactions or other hypersensitivity responses, further studies were carried out in which taxol was administered only after premedication with steroids (such as dexamethasone), antihistamines (such as diphenhydramine), and $H_2$antagonists (such as cimetidine or ranitidine), and the infusion time was extended to 24 hours in an attempt to eliminate the most serious allergic reactions. Various Phase I and Phase II study results have been published utilizing 24-hour infusions of taxol with maximum total dosages of 250 $mg/m^2$, generally with the course being repeated every 3 weeks. Patients were pretreated with dexamethasone, diphenhydramine, and cimetidine to offset allergic reactions. See Einzig, et al., "Phase II Trial of Taxol in Patients with Metastatic Renal Cell Carcinoma." *Cancer Investigation,* 9(2) 133–136 (1991), and A.

B. Miller et al., "Reporting Results of Cancer Treatment," *Cancer,* Vol. 47, 207-214 (1981).

Koeller et al., in "A Phase I Pharmacokinetic Study of Taxol Given By a Prolonged Infusion Without Premedication." *Proceedings of ASCO,* Vol. 8 (March 1989), recommends routine premedication in order to avoid the significant number of allergic reactions believed to be caused by the cremaphor (polyethoxylated castor oil) vehicle used for taxol infusions. Patients received dosages ranging from 175 mg/m$^2$ to 275 mg/M$^2$.

Wiernik et al., in "Phase I Clinical and Pharmacokinetic Study of Taxol." *Cancer Research,* 47, 2486–2493 (May 1, 1987), also report the administration of taxol in a cremaphor vehicle by IV infusion over a 6-hour period in a Phase I study. Grade 3–4 hypersensitivity reactions incurred in 4 of 13 courses. The starting dose for the study was 15 mg/m$^2$ (one-third of the lowest toxic dose in dogs). Doses were escalated, and a minimum of 3 patients were treated at each dose level until toxicity was identified, and then 4–6 patients were treated at each subsequent level. The study concluded that neurotoxicity and leucopenia were dose-limiting, and the recommended Phase II trial dose was 250 mg/m$^2$ with premedication.

Other exemplary studies on taxol include: Legha et al., "Phase II Trial of Taxol in Metastatic Melanoma." Vol. 65 (June 1990) pp. 2478–2481; Rowinsky et al., "Phase I and Pharmacodynamic Study of Taxol in Refractory Acute Leukemias." *Cancer Research,* 49, 4640–4647 (Aug. 15, 1989); Grem et al., "Phase I Study of Taxol Administered as a Short IV Infusion Daily for 5 Days," *Cancer Treatment Reports,* Vol. 71 No. 12 (December, 1987); Donehower et al., "Phase I Trial of Taxol in Patients With Advanced Cancer," *Cancer Treatment Reports,* Vol. 71, No. 12, (December 1987); Holmes et al., "Phase II Study of Taxol in Patients (PT) with Metastatic Breast Cancer (MBC)." *Proceedings of the American Society of Clinical Oncology,* Vol. 10, (March, 1991), pp. 60. See also Suffness, "Development of Antitumor Natural Products at the National Cancer Institute." *Grann Monograph or Cancer Research,* 31 (1989) pp. 21–44 (which recommends that taxol only be given as a 24-hour infusion).

In addition to taxol, other forms such as its physiologically tolerated salts, and derivatives, analogs, mixtures and conjugates thereof may be used in the practice of this invention. Examples of derivatives or analogs of taxol are 2' and 7 positions substituted taxols disclosed by A. E. Mathew, et al. *Synthesis and evaluation of some water-soluble prodrugs and derivatives of taxol with antitumor activity,* J. Med. Chem. 35:145–51 (1992). An example of taxol conjugates useful in the practice of this invention are disclosed in R. B. Greenwald, et al., *Drug Delivery Systems: water soluble taxol* 2'poly(ethylene glycol) ester prodrugs-design and in vivo effectiveness,J. Med. Chem. 39:424–31 (1996). Examples of derivatives or prodrugs of 2' substituted taxol and camptothecin are disclosed in Peter D. Senter et al., *The Role of Rat Serum Carboxylesterase in the Activation of Paclitaxel and Camptothecin Prodrugs,* Cancer Research 56:1471–75 (1996). Additional examples of taxol prodrugs or derivatives can be found in G. I. Georg, et al., *Synthesis of biologically active taxol analogs with modified phenylisoserine side chains,* J. Med. Chem 35:4230–37 (1992); S. W. Mamber, et al., *Tubulin polymerization by paclitaxel (taxol) phosphate prodrugs after metabolic activation with alkaline phosphatase,* J. Pharmacol Exp. Ther. 274:877–83 (1995); S. Grover et al., *Differential effects of paclitaxel (Taxol) modified at positions C-2, C-7, and C-3' tubulin polymerization and polymer stabilization: identification of a hyperactive paclitaxel derivative,* Biochemistry 34:3927–34 (1995).

Local delivery of inhibitory amounts of therapeutic agents for the treatment of cell proliferation can be by a variety of techniques and structures that administer the agents at or near the proliferative site. Examples of local delivery techniques and structures are not intended to be limiting but to be illustrative of the techniques and structures available. Examples include local delivery catheters, site specific carriers, implants, direct injection, or direct applications.

Local delivery by a catheter allows the administration of a therapeutic agent directly to the proliferative site. Examples of local delivery using a balloon catheter are described in EP 383 492 A2 and U.S. Pat. No. 4,636,195 to Wolinsky. Additional examples of local, catheter-based techniques and structures are disclosed in U.S. Pat. No. 5,049, 132 to Shaffer et al. and U.S. Pat No. 5,286,254 to Shapland et al.

Generally, the catheter must be placed such that the therapeutic agent can be delivered at or near the proliferative site. Dosages delivered through the catheter can vary, according to determinations made by one of skill, but should be in amounts effective to create a cytotoxic or cytostatic effect at the proliferative site. Typically, these total amounts are less than the total amounts for systemic administration of the therapeutic agent. The therapeutic agents delivered through catheters typically should be formulated to a viscosity that enables delivery through a small treatment catheter, and should be formulated with pharmaceutically acceptable additional ingredients (active and inactive).

Local delivery by an implant describes the placement of a matrix that contains the therapeutic agent into the proliferative site. The implant may be deposited by surgery or other means. The implanted matrix releases the therapeutic agent by diffusion, chemical reaction, solvent activators, or other equivalent mechanisms. Examples are set forth in Lange, *Science* 249:1527–1533 (September, 1990). Often the implants may be in a form that releases the therapeutic agent over time; these implants are termed time-release implants. The material of construction for the implants will vary according to the nature of the implant and the specific use to which it will be put. For example, biostable implants may have a rigid or semi-rigid support structure, with therapeutic agent delivery taking place through a coating or a porous support structure. Other implants made be made of a liquid that stiffens after being implanted or may be made of a gel. The amounts of therapeutic agent or agents present in or on the implant may be in an amount effective to treat cell proliferation generally, or a specific proliferation indication, such as the indications discussed herein.

One example of local delivery of the therapeutic agent by an implant is use of a biostable or bioabsorbable plug or patch or similar geometry that can deliver the agent once place in or near the proliferative site. An example of such implants can be found in U.S. Pat. No. 5,429,634 to Narciso, Jr., incorporated by reference. A particular application of use of an implant according to the invention is treatment of cell proliferation in tissue that is not highly vascularized, as discussed briefly above. An example of such tissue is bone tissue. The difficulty in treating uncontrolled proliferative cell growth in bone tissue may be exemplified by the difficulties in treating bone tumors. Such tumors are typically refractory to treatment, in part because bone tissue is not highly vascularized. An implant in or near the proliferative site may potentially have localized cytotoxic or cytostatic effects with regard to the proliferative site.

Therefore, in one embodiment, the invention may be used to treat bone tumors.

Another example of local delivery by an implant is the use of a stent. Stents are designed to mechanically prevent the collapse and reocclusion of the coronary arteries. Incorporating a therapeutic agent into the stent may deliver the agent directly to or near the proliferative site. Certain aspects of local delivery by such techniques and structures are described in Kohn, *Pharmaceutical Technology* (October, 1990), incorporated by reference. Stents may be coated with the therapeutic agent or agents to be delivered. Examples of such techniques and structures may be found in U.S. Pat. No. 5,464,650 to Berg et al., U.S. Pat. No. 5,545,208 to Wolff et al., U.S. Pat. No. 5,649,977 to Campbell, U.S. Pat. No. 5,679,400 to Tuch, EP 0 716 836 to Tartaglia et al., all of which are incorporated by reference. Alternatively, the therapeutic agent loaded stent may be biorotable, i.e. designed to dissolve, thus releasing the agent in or near the proliferative site, as disclosed in U.S. Pat. No. 5,527,337 to Stack et al., incorporated by reference. The present invention can be used with a wide variety of stent configurations, including, but not limited to shape memory alloy stents, expandable stents, and stents formed in situ.

Amounts of the therapeutic agent or agents delivered by the stent can vary, according to determinations made by one of skill, but should be in amounts effective to create a cytotoxic or cytostatic effect at the proliferative site. Typically, these total amounts are less than the total amounts for systemic administration of the therapeutic agent. Appropriate release times can vary, but preferably should last from about 1 hour to about 6 months, most preferably from about 1 week to about 4 weeks. Formulations including the therapeutic agent for delivery of the agent via the stent can vary, as determinable by one of skill, according to the particular situation, and as generally taught herein.

Another example is a delivery system in which a polymer that contains the therapeutic agent is injected into the proliferative cells in liquid form. The polymer then cures to form the implant in situ. One variation of this technique and structure is described in WO 90/03768 to Donn, incorporated by reference.

Another example is the delivery of a pharmaceutical agent by polymeric endoluminal sealing. This technique and structure uses a catheter to apply a polymeric implant to the interior surface of the lumen. The therapeutic agent incorporated into the biodegradable polymer implant is thereby released at the proliferative site. One example of this technique and structure is described in WO 90/01969 to Schindler, incorporated by reference.

Another example of local delivery by an implant is by direct injection of vesicles or microparticulates into the proliferative site. These microparticulates may comprise substances such as proteins, lipids, carbohydrates or synthetic polymers. These microparticulates have the therapeutic agent incorporated throughout the microparticle or over the microparticle as a coating. Examples of delivery systems incorporating microparticulates are described in Lange, *Science*, 249:1527–1533 (September, 1990) and Mathiowitz, et al., *J. App. Poly Sci.* 26:809 (1981), incorporated by reference.

Local delivery by site specific carriers describes attaching the therapeutic agent to a carrier which will direct the drug to the proliferative site. Examples of this delivery technique and structure include the use of carriers such as a protein ligand or a monoclonal antibody. Certain aspects of these techniques and structures are described in Lange, *Science* 249:1527–1533, incorporated by reference.

Local delivery also includes the use of topical applications. An example of a local delivery by topical application is applying the therapeutic agent directly to an arterial bypass graft during a surgical procedure. Other equivalent examples will no doubt occur to one of skill in the art.

Finally, there are other equivalent techniques and structures for delivering the therapeutic agent besides those techniques discussed above. Such techniques and structures will no doubt occur to one of ordinary skill, and are within the scope of this invention.

EXAMPLES

Example 1

In Example 1, use of a stent according to the invention is demonstrated. Following the general guidance of Berg et al. (U.S. Pat. No. 5,464,650), and the specific guidance in Example 6 of Berg et al., a dispersion of 9-nitro 20(S) camptothecin is mixed with a 1% poly(L-lactic acid) solution in chloroform. This solution is then used to coat Wiktor type stents, in accordance with the procedure set forth in Berg et al.

The coated stents are then delivered in an artery at or near a tumor site, and deployed to supply 9-nitro 20(S) camptothecin to the tumor site in a localized fashion.

Example 2

In Example 2, use of a stent according to the invention is demonstrated. Following the general guidance of Berg et al. (U.S. Pat. No. 5,464,650), and the specific guidance in Example 6 of Berg et al., a dispersion of mitoxantrone is mixed with a 1% poly(L-lactic acid) solution in chloroform. This solution is then used to coat Wiktor type stents, in accordance with the procedure set forth in Berg et al.

The coated stents are then delivered in an artery at or near a tumor site, and deployed to supply mitoxantrone to the tumor site in a localized fashion.

Example 3

In Example 3, use of a stent according to the invention is demonstrated. Following the general guidance of Berg et al. (U.S. Pat. No. 5,464,650), and the specific guidance in Example 6 of Berg et al., a dispersion mixture of 9-nitro 20(S) camptothecin and mitoxantrone is mixed with a 1% poly(L-lactic acid) solution in chloroform. This solution is then used to coat Wiktor type stents, in accordance with the procedure set forth in Berg et al.

The coated stents are then delivered in an artery at or near a tumor site, and then deployed to supply 9-nitro 20(S) camptothecin and mitoxantrone to the tumor site in a localized fashion.

Example 4

In Example 4, use of a catheter according to the invention for treating cell proliferation in an artery resulting from a heart transplant is demonstrated. Following the general guidance of Shaffer et al. (U.S. Pat. No. 5,049,132), and the specific guidance found at column 6 of Shaffer, a drug delivery catheter is assembled, and the catheter tip is guided to the proliferative site in the artery. Once the treatment balloon is located at or near the proliferative site, a dispersion of 9-nitro camptothecin is injected into the drug delivery lumen and then is forced out of the tip of the balloon catheter tip according to Shaffer. In this manner, the 9-nitro 20(S) camptothecin dispersion is delivered locally to treat the proliferative site.

Example 5

In Example 5, use of a catheter according to the invention for treating cell proliferation in an artery resulting from a heart transplant is demonstrated. Following the general guidance of Shaffer et al. (U.S. Pat. No. 5,049,132), and the specific guidance found at column 6 of Shaffer, a drug delivery catheter is assembled, and the catheter tip is guided to the proliferative site in the artery. Once the treatment balloon is located at or near the proliferative site, a solution of etoposide is injected into the drug delivery lumen and then is forced out of the tip of the balloon catheter tip according to Shaffer. In this manner, the etoposide solution is delivered locally to treat the proliferative site.

Example 6

In Example 6, use of a catheter according to the invention for treating cell proliferation in an artery resulting from a heart transplant is demonstrated. Following the general guidance of Shaffer et al. (U.S. Pat. No. 5,049,132), and the specific guidance found at column 6 of Shaffer, a drug delivery catheter is assembled, and the catheter tip is guided to the proliferative site in the artery. Once the treatment balloon is located at or near the proliferative site, a dispersion mixture of 9-nitro camptothecin and etoposide is injected into the drug delivery lumen and then is forced out of the tip of the balloon catheter tip according to Shaffer. In this manner, the 9-nitro 20(S) camptothecin and etoposide dispersion is delivered locally to treat the proliferative site.

Example 7

In Example 7, use of a catheter according to the invention for treating cell proliferation in other indications is demonstrated. These other indications include restenosis, various types of cancers such as primary tumors, insults to body tissue due to surgery, diseases that produce fibrosis of tissue, repetitive motion disorders, and disorders of tissues that are not highly vascularized.

Following the general guidance of Shaffer et al. (U.S. Pat. No. 5,049,132), and the specific guidance found at column 6 of Shaffer, a drug delivery catheter is assembled, and the catheter tip is guided to the proliferative site. Once the treatment balloon is located at or near the proliferative site, a dispersion mixture of 9-nitro camptothecin is injected into the drug delivery lumen and then is forced out of the tip of the balloon catheter tip according to Shaffer. In this manner, the 9-nitro 20(S) camptothecin dispersion is delivered locally to treat the proliferative site.

It is apparent to those skilled in the art that various modifications and variations can be made in the implants, stents, apparatus, methods and kits of the present invention without departing from the spirit or scope of the invention. Thus, it is intended that the present invention cover the modifications and variations of this invention provided they come within the scope of the appended claims and their equivalents.

What is claimed is:

1. A method for treating restenosis of a blood vessel by using a water-insoluble camptothecin compound in combination with a stent to treat tissue of the blood vessel, the method comprising:

coating a stent with a water-insoluble camptothecin compound dispersed in 1% poly(L-lactic acid) solution in chloroform inserting the stent into a blood vessel;

supporting the blood vessel with the stent to mechanically prevent the collapse and reocclusion of the blood vessel; and contacting tissue forming the blood vessel with the water-insoluble camptothecin compound, wherein the water-insoluble camptothecin compound is selected from the group consisting of 9-nitro-20(S)-camptothecin and 9-amino-20(S) camptothecin in a concentration sufficient to reduce restenosis In the blood vessel.

2. The method of claim 1, wherein inserting the stent includes inserting the stent adjacent a potential coronary, carotid or cerebral restenotic lesion.

3. The method of claim 1, where the blood vessel is selected from the group consisting of an artery, a vein, and a capillary.

4. The method of claim 1, wherein the water-insoluble camptothecin compound is 9-nitro-20(S)-camptothecin.

5. The method of claim 1, wherein the body of the stent is selected from the group consisting of a shape memory alloy stent, an expandable stent, and a stent formed in situ.

\* \* \* \* \*